United States Patent [19]
Kirkpatrick et al.

[11] 4,131,114
[45] Dec. 26, 1978

[54] ORTHOPEDIC CAST

[75] Inventors: Harold B. Kirkpatrick, Easton, Conn.; Edward C. Distler, Warminster, Pa.; Marvin Menzin, Lexington, Mass.

[73] Assignee: Reichhold Chemicals, Inc., White Plains, N.Y.

[21] Appl. No.: 764,199

[22] Filed: Jan. 31, 1977

Related U.S. Application Data

[62] Division of Ser. No. 536,254, Dec. 24, 1974, Pat. No. 4,020,832.

[51] Int. Cl.² ............................................. A61F 13/04
[52] U.S. Cl. ............................................. 128/90; 427/2; 260/77.5 AP
[58] Field of Search .................... 128/90; 206/219; 260/77.5 AP

[56] References Cited

U.S. PATENT DOCUMENTS

| 3,301,252 | 1/1967 | Mahoney, Jr. | 128/90 |
| 3,375,822 | 4/1968 | Rose | 128/90 |
| 3,378,511 | 4/1968 | Newton | 260/77.5 AP |
| 3,728,206 | 4/1973 | Buese | 128/90 |
| 3,847,859 | 11/1974 | Olstowski | 260/77.5 AP |
| 4,052,282 | 10/1977 | Kubushiro | 128/90 |

FOREIGN PATENT DOCUMENTS 1245937  9/1971  United Kingdom ............ 128/90

Primary Examiner—Dalton L. Truluck
Assistant Examiner—Jerome D. Stremcha
Attorney, Agent, or Firm—Brooks, Haidt, Haffner & Delahunty

[57] ABSTRACT

Spool of tape and all necessary resin-forming reactant liquids are packaged in a "one-shot", disposable container for delivery to a physician who mounts the unopened package on an activator machine which spins it in successive operational stages to first activate the reactant liquids by mixing in a mixing region of the package and then wet the tape with the activated liquid by centrifuge, subsequent centrifuging removing excess liquid, whereupon the package is opened and the spool of tape, now damp with the curing resin thereon, is removed for winding on the patient's body to form a polyurethane resin orthopedic cast which hardens within minutes in air and without additional curing procedures. Preferred reactant liquids, plasticizers, and catalysts are disclosed, which have long shelf-life within the package. Package of materials includes special container having inner container containing one reactant liquid; means for opening inner container upon mounting package on activator machine to permit its contents to mix with other reactant liquid disposed at the bottom of the outer container; paddle members for mixing the reactants responsive to intermittent spinning of the package while in a tilted position; and an interior partition configured both to provide a funnel for channeling the polymerizing liquid into a hollow core of the tape spool, and to provide a peripherally extending excess liquid collection region surrounding and extending below the tape spool.

1 Claim, 19 Drawing Figures

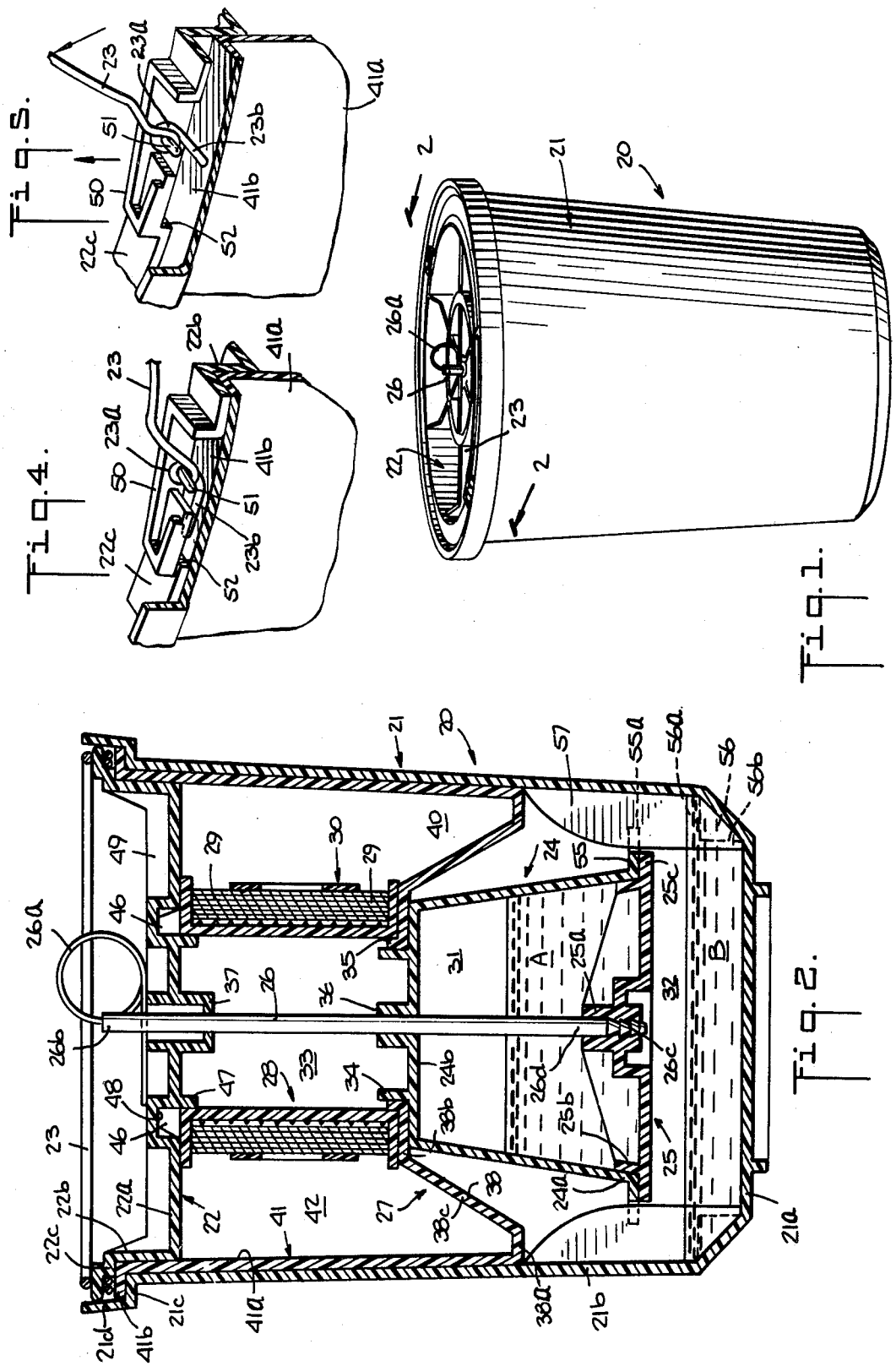

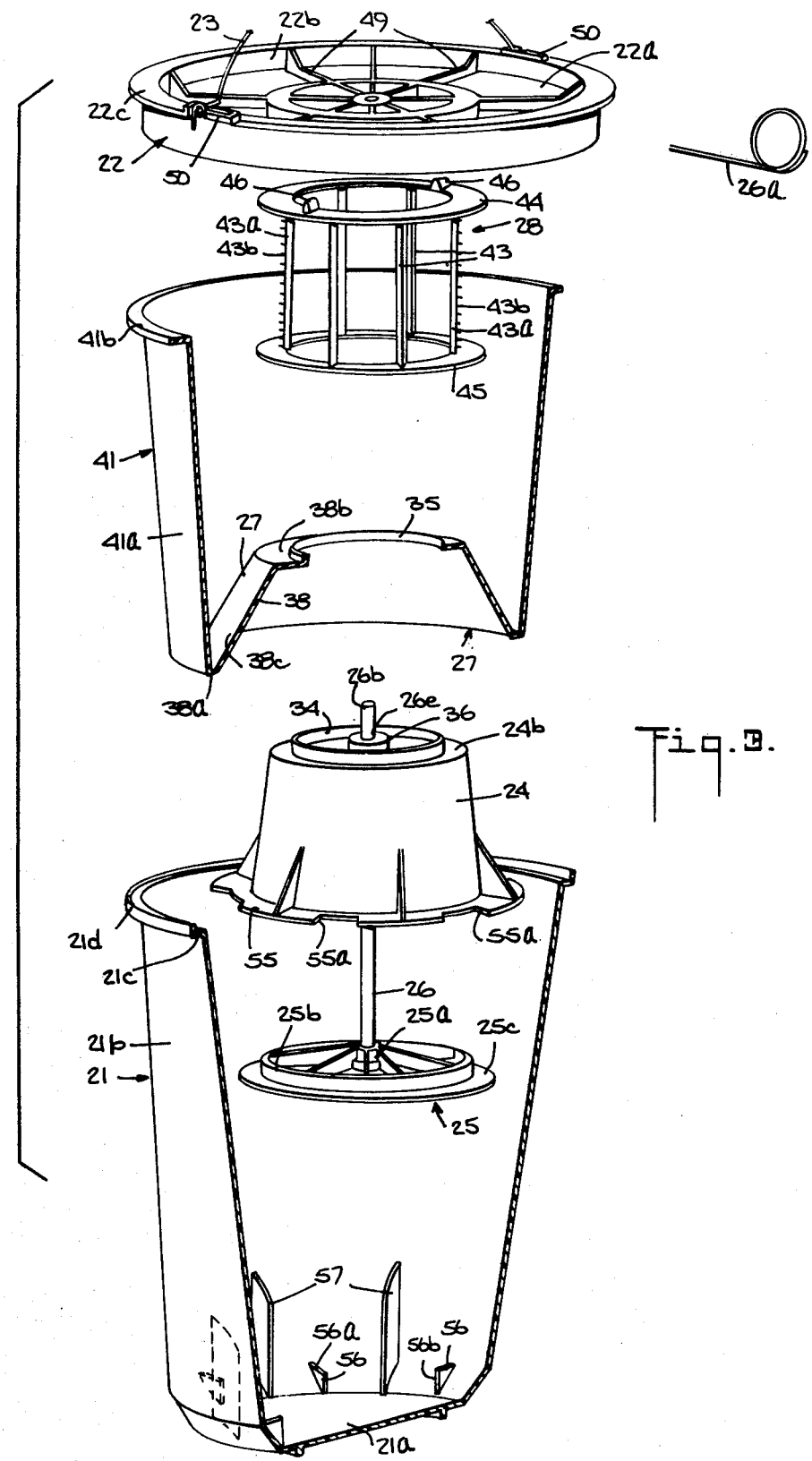

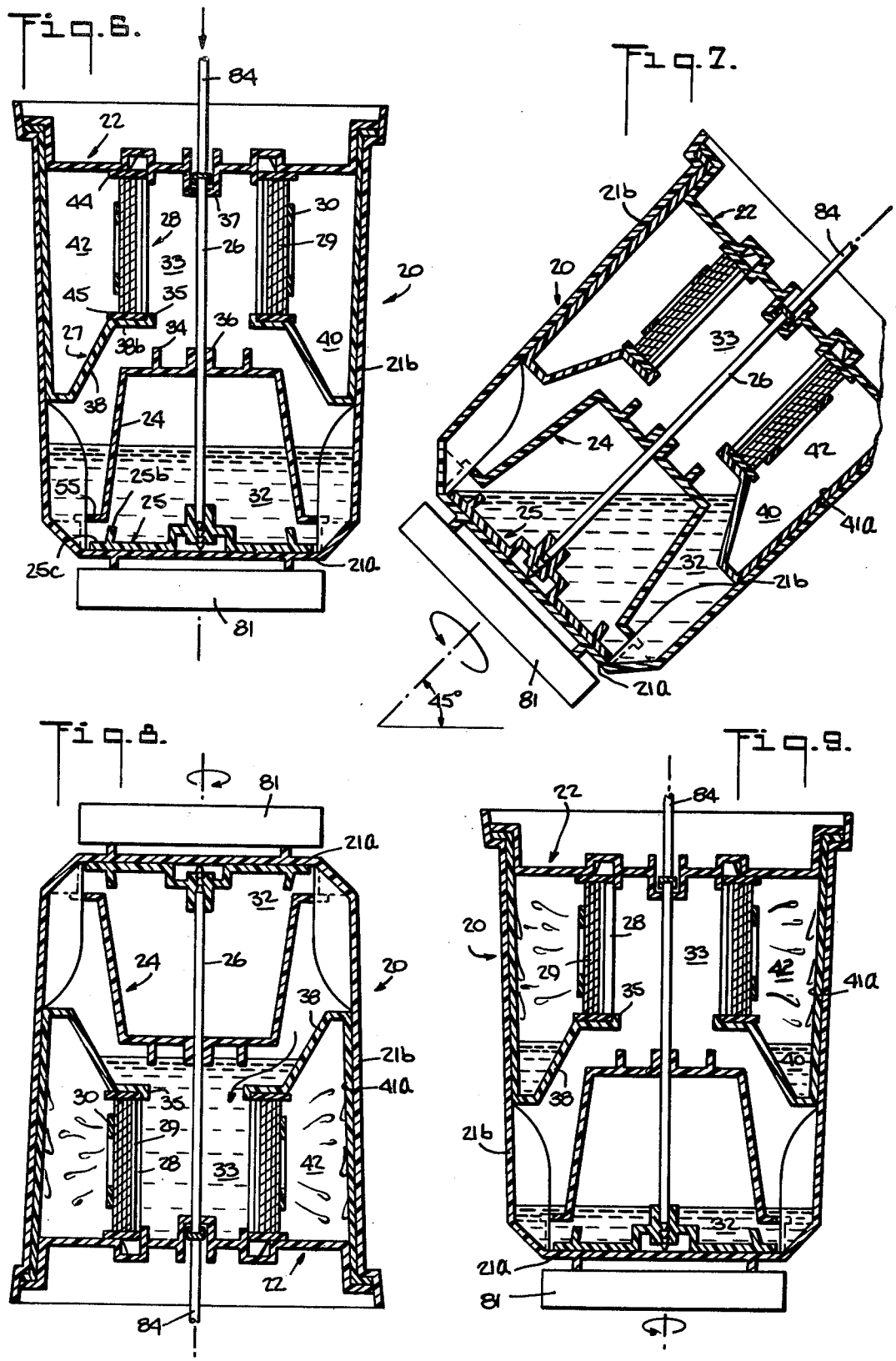

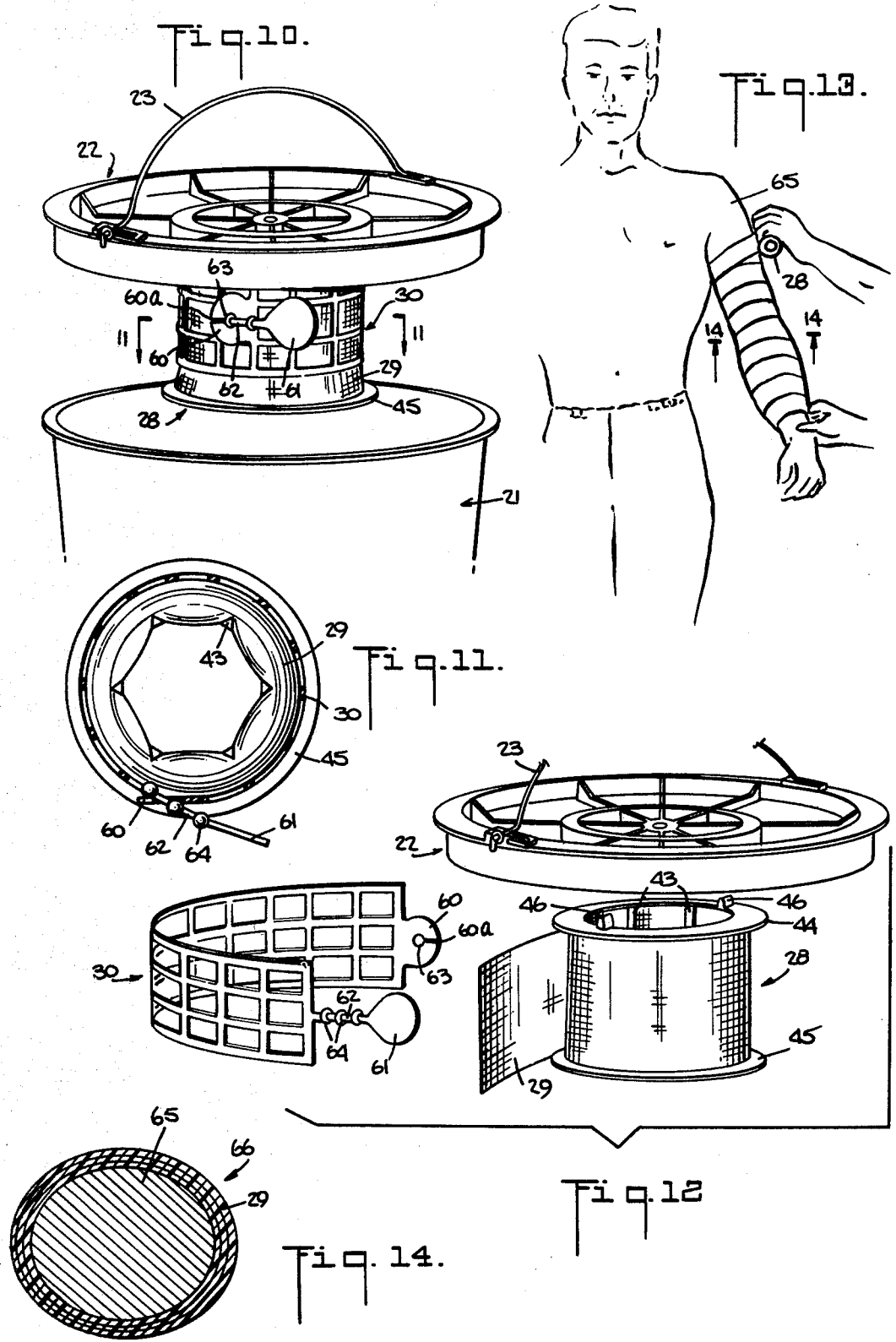

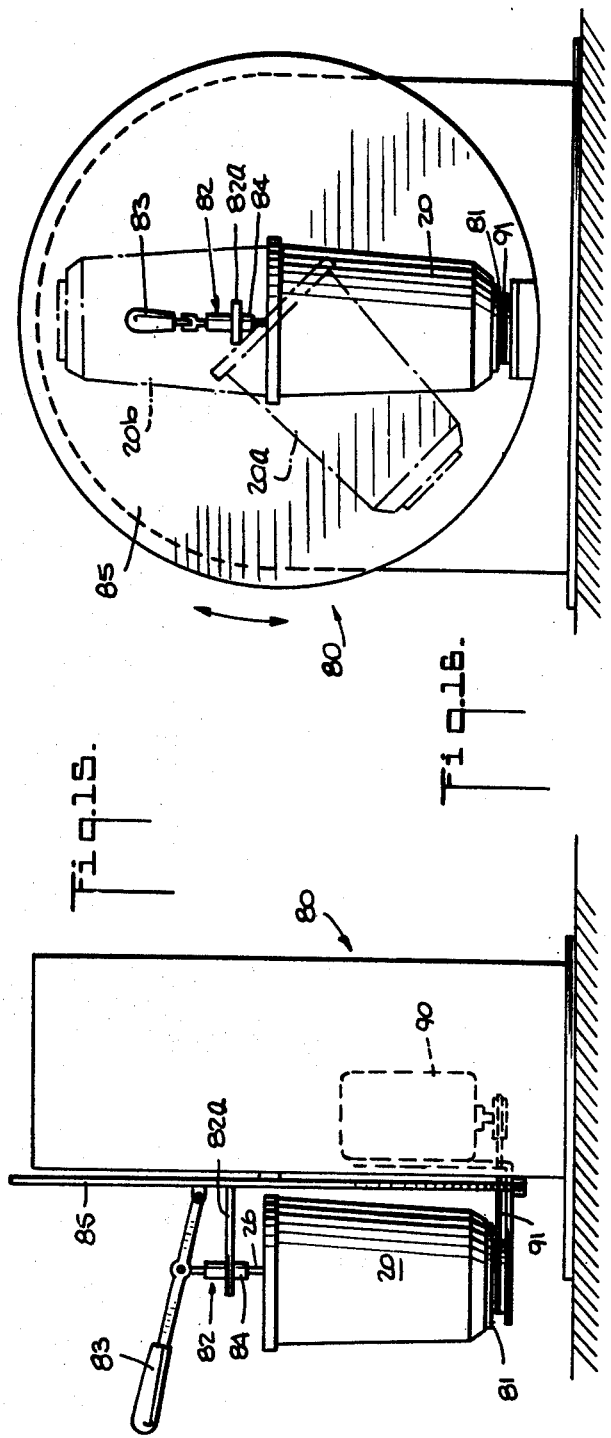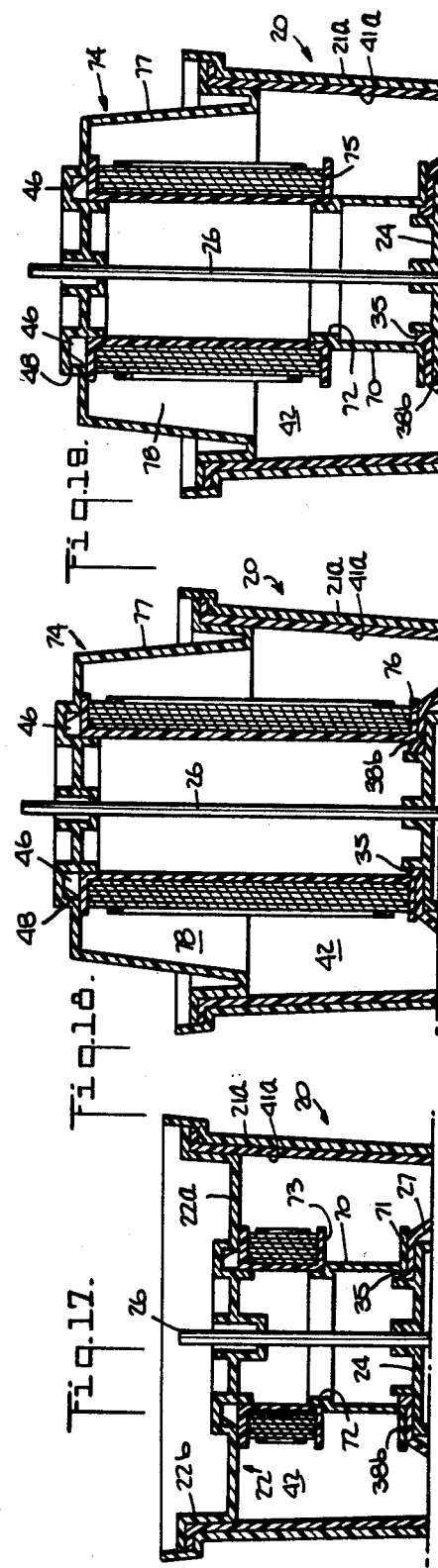

ORTHOPEDIC CAST

This is a division of application Ser. No. 536,254 filed Dec. 24, 1974 now U.S. Pat. No. 4,020,832 issued May 3, 1977.

This invention relates to techniques for making orthopedic casts of resin material, and more particularly to a method and means for packaging and thereafter activating the resin-forming materials and applying the activated materials to a tape for application to a body member to form the cast thereon.

Orthopedic casts have been made of various curable foamed and unfoamed resin materials which are activated either prior to or after application to the body member in a variety of ways, the purpose of such so-called "plastic casts" being to overcome the known disadvantages of the more conventional plastic of Paris cast. However, either in the manner in which they must be applied to the body member, or in which they must be activated to commence the polymerization reaction, or in the characteristics of the resulting orthopedic cast, such techniques as are known for preparing and applying plastic orthopedic casts are not entirely satisfactory.

For example, in U.S. Pat. No. 3,656,475 (Hanrahan, Jr.) there is disclosed a plastic orthopedic cast which is applied to the injured body member in the form of a tubular knitted fabric base sleeve drawn over the body member. An outer portion of the sleeve is impregnated with a curable liquid resin composition by spraying a coating of an activated and therefore already curing polyurethane resin-forming composition thereon. However, for spraying or coating technique is sometimes messy, and the use of a sleeve as a base fabric does not approximate the familiar manner of applying plastic casts using a roll of tape whose tension and firmness of application can be more readily controlled by the physician as he wraps the tape on the patient's body and the resulting casts are not breathable. In the technique disclosed in U.S. Pat. No. 3,301,252 (Mahoney,Jr.) the patient's limb is first wrapped using a suitable gauze tape, and thereafter a self-curing, foamed-in-place polyurethane foam material is sprayed thereover. However, the application technique is unfamiliar to the physician, and foamed plastic casts are bulky, and sometimes insufficiently rigid when not suitably reinforced.

U.S. Pat. Nos. 3,421,501 (Beightol) and 3,618,599 (Beightol) describe ultra-violet light curable or ultrasonic energy curable polymers as first being impregnated into woven or non-woven fabric which may be in the form of a tape. The impregnated tape is then wound on to the body member in a conventional manner, after which the taped body member must be exposed to the ultra-violet irradiation or ultrasonic energy, as the case may be, to cure the cast in place. However, the ultraviolet curable resins emit an offensive odor to which the patient is subjected during the curing process, and both techniques are emotionally disconcerting to the patient because of the need for exposure of his body to such ancillary energy-radiating equipment.

U.S. Pat. No. 3,630,194 (Boardman) proposes that the tape from which an orthopedic cast will be made should be impregnated with a water-activated, curable resin composition. The tape is applied to the patient's limb in rolled form after dipping the roll in water, which may contain the catalyst, and squeezing the roll to remove excess water.

Where the completed plastic orthopedic cast is to be air-pervious, many of the known techniques for applying the resin-forming materials to a porous or woven base do not ensure that the interstices of the material will not be blocked by the cured resin.

It is therefore apparent that difficulties experienced when practising one or another of the previous techniques may include the difficulty of applying a uniform coating of the resin-forming materials on the base fabric; the difficulty of applying a correct quantity of such materials on the fabric; and uncertainty regarding either the correct proportions of the resin-forming materials to be used, or the correct time duration and evenness of exposure of unactivated resin-coated casts to the heat, ultrasound, or ultra-violet radiation curing device to which the formed case must be subjected. Moreover, the physician or technician who must prepare or apply such casts has many other primary duties and therefore desires that preliminary preparation be as uncomplicated as possible, and the application procedure be clean, convenient, and free from possible mistake.

It is therefore intended by the present invention to provide to the physician, for use in forming an orthopedic cast, a spooled tape which he may wind on the patient in the manner to which he is accustomed when applying plaster casts, and which is uniformly coated with an adequate though limited amount of pre-proportioned reactant resin materials which are already activated and therefore in a curing liquid state, so that the curing will be completed at room temperature in a matter of minutes after the cast has been applied. Thus, the physician can control the tension and placement of the tape as it is applied to the patient, after which the cast automatically hardens without the need for subjecting the cast and patient to heat, ultra-violet light, sonic energy, or similar curing devices.

In furthering these objects it is believed advantageous, and is therefore additionally intended that all of the necessary resin-forming reactant liquids be preproportioned and packaged together with a spool of tape, having a convenient length of tape thereon, and delivered for a single use by the physician in a throw-away container. The resin-forming liquids should be activated immediately before the time of their intended use, and the tape should be properly wetted therewith, while the chemicals and the tape remain within the unopened package. Such provides assurance that the tape will be coated properly, and independently of individual skills or training and without possibility for error in either the amount or the proportions of the resin-forming constituents. It also avoids messiness when mixing and using the chemicals.

Packages of resin-forming liquids which are activated and applied to tape within a package are known for other uses. For example, U.S. Pat. No. 3,864,492 (Lappala) shows such a package for preparing adhesive strips for manufacturing uses. However, extraction of excess resin from the tape as necessary for present purpose is not achieved, nor is the wetted tape taken from the package in roll form.

Such activation and wetting of the tape must be done quickly and conveniently, as well as with reproducible quality. Moreover, since a number of packages will be delivered at one time to the physician's office or to a hospital for use at future times, the packaged chemicals must have long shelf life under unusual storage conditions, and must withstand reasonable temperature changes and agitation during shipping. The invention, therefore, involves the discovery of specific resin-forming liquid materials and compositions for the purpose.

The invention also contemplates that the actions of mixing the chemicals and wetting the tape will be performed on relatively inexpensive bench-type machine, whose cycles are measured and repetitive, which will be a part of the standard equipment in hospitals or doctors' offices. Although the the machine itself is not, the machine mixing and wetting cycles are contemplated by the present invention.

Moreover, to adapt the package for such mixing and wetting actions as the machine will perform, the invention further contemplates the use of a container having particular features, and particular disposition and orientation within the container of the tape and each of the resin-forming reactant liquids.

Containers having particular features for mixing purposes are known, but none appear to have features for serving the purposes of the present invention. That is, U.S. Pat. No. 3,521,745 (Schwartzman) shows a single package in which initially separate ingredients are mixed by perforating separate rupturable compartments using a bellows feature of the outer container and an interiorly disposed plunger, and U.S. Pat. No. 3,321,097 (Solowey) discloses a bottle having separate compartments which may be placed in communication upon opening a valve using a valve stem operable from the exterior of the bottle. In U.S. Pat. No. 3,321,917 (DeSanto et al.) one of the components to be mixed is initially contained in a separate interior container-like structure which provides a funnel-shaped partition leading to a narrow mouth opening of the structure at its upper end, the narrow mouth opening being initially closed by a vertically movable valve whose stem is attached to the upper end wall of an outer container. The valve is opened by expanding an accordion-like pleated wall portion of the outer container, which causes the valve stem to move upwardly. The package is then inverted to achieve mixing of a first liquid component contained in the interior container-like structure with another liquid component within the outer container. None of these packages or containers includes a tape or tape spool, nor contemplates the mounting or wetting of a roll of tape therein. In these and other respects the container and package of the present invention appear to be different in overall arrangement and features from any known containers or packages.

Describing the invention generally, a length of liquid-pervious tape, preferably woven or knitted fiberglass tape, is wound on a cage-like cylindrical spool which is removably mounted within a container, the tape spool and the several parts of the container as will be described being made from a plastic material such as polypropylene or polyethylene or any other material which is not rapidly attacked by any of the resin-forming reactant materials which are also placed in the container. The tape spool is actually mounted and extends between the top closure of the container and the upper end of an inverted funnel-like, peripherally extending partition wall which divides the interior of the container into essentially two regions, i.e. a lower "mixing" region and an upper "wetting and extraction" region.

The open circular area at the underside of the cylindrical tape spool surrounds the narrow neck opening provided by the upper end of the funnel-shaped partition wall on which the spool is mounted, and the similar area at the upper end of the cylindrical hollow core of the spool is closed by the container top closure so that, when the container is inverted and spun on its central axis as will be described, liquid poured through the narrow neck opening of the funnel into the core of the tape will be centrifuged through the cage-like tape spool and the liquid-pervious tape, thereby wetting the tape with the liquid. The outer diameter of the spool of tape is smaller than the inner diameter of the container, thus providing a peripherally extending collection region for excess liquid centrifuged through the tape. When the container is subsequently unrighted and again spun on its axis, any excess liquid within the tape and which would otherwise span across and close the interstices of the material of which the tape is made, is extracted by centrifugal action and is initially deposited on the interior wall of the container within this peripheral liquid collection region. When the spinning is stopped, the extracted excess liquid flows by gravity downwardly on the inner peripheral wall surface of the container and it is collected in a V-shaped peripheral zone formed by the exterior surface of the referred to inverted funnel-shaped partition wall and the inner wall surface of the container, to which the outwardly projecting lower end of the partition wall extends.

The "container" thus far described is actually an outer container of the package unit, there being an inner container in which a measured quantity of one of the reactant liquids of the polymer system is stored before mixing with the correct quantity of a second reactant liquid which lies on the bottom of the outer container. Although the inner container might be in the form of a separate package of thin plastic material which is simply placed in the aforementioned lower region of the outer container, in the preferred embodiment it is a rigid plastic, inverted cup-like container placed within the mixing region and having a ring-shaped flange on its inverted bottom wall which is press-fit within and from the underside of the aforementioned narrow neck opening of the funnel-shaped partition wall. The open mouth of this inner container, which faces downwardly, functions as a valve seat and is closed by a flat, valve-like closure which is press fit into the open mouth to form a liquid-tight seal.

The inner container valve is opened by downward movement of a valve stem of package activator rod. The rod passes through the inverted bottom of the inner container, thence through the core region of the cylindrical tape spool, and through the top closure on the outer container, so that the rod projects exteriorly and may be operated by pressing it downwardly from the exterior of the package to open the valve on the inner container. The rod fits tightly as it passes through the bottom of the inner container and through the outer container closure, thus providing liquid-tight seals at these locations.

The downward movement of the valve stem rod will be effected by a manually operated toggle clamp on an activator machine on which the package is mounted when an orthopedic cast is to be made. The container will be placed on a spin table, and pressed downwardly thereagainst by the referred to toggle clamp which engages the top of the upwardly projecting valve stem rod.

Upon opening the inner container valve the contained reactant liquid is released to flow to the bottom of the outer container, to mix with the second reactant liquid. After thorough mixing of these liquids on the activator machine, the entire package will be inverted by the machine so that the mixed liquids will flow via the aforementioned funnel into the core of the tape spool, and it becomes apparent that the inner container must be removed from its seating engagement within the narrow neck opening of the funnel to permit the liquid to flow therethrough. For this purpose, the relative tightnesses of fits of the valve stem rod, the inner container valve, and the inner container bottom ring within their respective openings are made such that, upon downward movement of the valve stem rod, the still closed inner container will be unseated first, and moved downwardly away from the funnel neck opening to open the latter. During the downward movement an outwardly projecting peripheral rim on the downwardly facing end of the inner container abuts against several upwardly projecting and annularly spaced apart stops at the bottom of the outer container so that further downward movement of the valve stem rod forces the inner container valve to open.

Although the reactant liquids might be thoroughly mixed by spinning the valve stem rod from the exterior of a stationary outer container using the inner container and valve members as a paddle, or by spinning the outer container relative to a stationary valve stem rod, valve member, and inner container, in view of the subsequent centrifuge wetting and extracting operations which will also be conducted on the activator machine, it is believed preferable that the entire package be rotated, preferably intermittently, on its longitudinal axis to mix the reactants. To assist this mixing action the interior of the outer container adjacent to its bottom end has fixed, annularly spaced apart, vertical paddles over which the mixing liquids will course during mixing rotation of the package. As will be seen, spinning of the package during the mixing step is conducted while the central longitudinal axis of the package is tilted at an oblique angle, preferably 45°, to the horizontal, such tilting also being done by the activator machine.

After mixing, the activator machine automatically increases the tilt angle to 180°, in which the package is inverted, so that the mixed liquids flow by gravity through the funnel and into the core area of the cylindrical tape spool, as aforesaid. The machine then spins the package at high speed, centrifuging the liquid through the liquid-pervious tape material. After such wetting of the tape the machine automatically returns the package to its upright position, in which it is again spun at high speed to extract by centrifugal action any excess liquid within the interstices of the tape material.

The package is then removed from the machine, and its top closure is opened, whereupon the wetted tape is ready for use. In the preferred embodiment the tape spool has a press-fit connection to the underside of the closure so that the spool is lifted out of the container as its closure is removed. The spool may remain on the closure or be separated therefrom for use, as desired. Of course, the spool need not be connected to the underside of the closure, but might simply be revealed within the container when the closure is removed.

In preferred embodiments the reactant liquids are resin-forming monomers, these being a liquid diisocyanate as a first component of the system, including aromatic diisocyanates such as toluene diisocyante (TDI), aliphatic or cycloaliphatic diisocyanates, or preferably methylene diphenyl diisocyanate (MDI) in any of its several forms, and a polyol as the second component, preferably of dihydric or trihydric alcohol such as the reaction product of diethylene or triethylene glycol, butylene glycol, or any polyalkylene glycol, especially those having from two to four carbon atoms in the alkylene group, and an alkylene oxide, preferably having two to four carbon atoms in the molecule, such as ethylene oxide, propylene oxide, or butylene oxide. A preferred polyol is the reaction product of glycerine and propylene oxide, the material having an average molecular weight of approximately 260. Although the positions might be reversed, the diisocyanate component is placed in the cup-like inner container of the package, and the polyol component is placed in the bottom of the outer container.

A plasticizer can be used and is preferably a short chain dialkyl phthalate such as dibutyl phthalate, although a longer chain plasticizer such as dioctyl phthalate can be used. The plasticizer is preferably initially added to the polyol, but all or a portion of the plasticizer could be initially mixed and stored with the diisocyanate component, or the use of a separate plasticizer constituent as such could be eliminated by substituting a more flexible or longer chain polyol for the aforementioned more rigid or short chain polyols.

The catalyst used in preferred embodiment is an organo-metallic compound such as organo-tin compounds for example dibutyl tin dilaurate, although other catalysts could be used, including amines such as triethylene diamine, or metal salts of organic acids, such as calcium octoate. Preferably the catalyst is dibutyl tin dilaurate. The catalyst is mixed and stored with the polyol in the package prior to polymerization.

These and other objects, features and advantages of the invention will become more apparent from the following detailed description of the invention, when taken together with the accompanying drawings, in which:

FIG. 1 is a perspective showing of an orthopedic cast-making package in accordance with the invention;

FIG. 2 is an enlarged cross-sectional view of the package as seen from lines 2—2 of FIG. 1;

FIG. 3 is a fragmentary and perspective exploded view showing the container components of the package, to further illustrate its details;

FIGS. 4 and 5 are enlarged fragmentary showings, partially in cross section, to illustrate a feature of the package of FIG. 1;

FIGS. 6–9 are cross-sectional showings of the package handling and method steps in accordance with the invention to prepare a tape within the package for use in making an orthopedic cast;

FIG. 10 is a perspective showing of the prepared tape as it is being removed from the package;

FIG. 11 is a cross-sectional view of the wetted spool of tape as seen from lines 11—11 in FIG. 10;

FIG. 12 is an exploded perspective showing of the spooled tape and closure sub-assembly in the package;

FIG. 13 is an illustration of how an orthopedic cast is formed using the wetted spool of tape provided by the invention;

FIG. 14 is an enlarged cross-sectional showing of an orthopedic cast on a body member, as made using tape prepared in accordance with the invention;

FIG. 15 is a side-elevational view, to a reduced scale, showing how a package in accordance with the invention is activated on an activator machine;

FIG. 16 is a front elevational view of the machine of FIG. 15, showing the several tilt positions of the package during activation; and FIGS. 17, 18 and 19 are respective fragmentary cross-sectional views of several packages to illustrate various modified forms of the tape spool and closure sub-assembly for accommodating various tape sizes.

Referring first to FIGS. 1–3, an orthopedic cast-making package, containing all of the necessary materials for making a resin-type cast, is indicated by reference numeral 20. FIGS. 1 and 2 show the package and its contents as delivered to a hospital or physician's office for later use in making only one cast, after which the container and any residue are discarded. As previously noted, the package will remain closed, even while its contents are being activated and readied for use, and will be opened only when it is time to form the cast on the patient.

The cast will be formed by winding a bandage or tape onto the body member of the patient, the tape being damp with the resin-forming liquid materials which are already activated and which will continue to cure in air at room temperature during the several minutes it takes to form the cast, after which the polymerizing liquid will harden, and rigidify the tape and thus the cast. For these purposes a two-component resin system was selected, the preferred reactant constituents being methylene diphenyl diisocyanate modified to remain in the liquid phase at room temperature (77° F.) such as Isonate 143-L made by The Upjohn Company of Kalamazoo, Michigan, and a polyol such as Polylite 34-402 made by Reichhold Chemicals, Inc. of White Plains, New York, and which is a polyhydric alcohol. The proportions of these reactant monomers are 100 parts by weight of the diisocyanate to 50 parts by weight of the polyol. Dibutyl phthalate, such as 48-550 also made by Reichhold Chemicals, Inc., in the amount of 50 parts by weight is added to the polyol, although all or any portion of this plasticizer could be added to the diisocyanate component. The catalyst is dibutyl tin dilaurate, such as T-12 made by M&T Chemicals Co. Division of American Can Company, New York, N.Y., in an amount ranging from about 0.03 to about 0.30 preferably 0.06 parts by weight added to the polyol component. Thus, in the preferred embodiment in which all of the plasticizer is contained in the polyol, the ratio of the diisocyanate material to the polyol and plasticizer material is about 1:1 by weight.

The tape which will be wetted with the reacting monomers is preferably of knitted or woven materials, so that the cast will be air-permeable when formed. The preferred tape material is made of interlaced glass yarns which are first desized and then coated with a coupling agent or finish, such as the material described in U.S. Pat. No. 3,793,686 (Nisbet et al.) and obtainable from Carolina Narrow Fabric Co. of Winston-Salem, North Carolina.

The total amount of reactant liquid materials A and B which will be contained in the package 20 depends, of course, upon the length and width, and to some extent the absorbency, of the tape to be contained in the package. For example, the package 20 to be described in connection with FIGS. 1–16 contains a five-foot length of nominally two inch wide (actual dimension one and three-quarter inch) tape of the type described, and the package 20 contains a total of about five fluid ounces of the reactant liquids A and B, which provides an excess quantity of liquid to ensure that the tape is thoroughly wetted without recycling any centrifuged excess liquid back to the core of the tape spool during the contemplated centrifuge wetting operation.

Referring again to the drawings, FIGS. 2 and 3 show that the package 20 has an outer container 21 having a top closure 22 which has a handle 23; an inverted cup-like inner container 24 having a valve 25 which normally closes its downwardly facing open end 24a; a vertically movable valve stem 26 for opening the valve 25, the stem having a removable cotter pin 26a; a partition wall member 27; and a tape spool 28; which together serve as a packaging means for the materials for making an orthopedic cast. The cast-making materials are the two reactant liquid materials, A and B of the resin system and the length of tape 29 which is wound on the tape spool 28. The packaging means also includes a plastic mesh retainer band 30 (see also FIGS. 10–12) which holds the wound tape 29 in place.

The materials from which these packaging components are made are such as will not be attacked by the constituents of the reactant liquids A or B, particularly the diisocyanate. Preferably, and excepting for the valve stem 25 and handle 23 which are made of metal, they are all of polypropylene plastic material.

The reactant liquids A and B, which will react and begin to polymerize when mixed together, are stored separately within the package, at least one of them being in a liquid-tight compartment. In the embodiment shown, reactant material A is packaged in the liquid-tight enclosure 31 formed by the interior of the inner container 24 and its normally closed valve 25, and reactant material B is placed in the bottom interior region 32 of the outer container 21, adjacent to its bottom wall 21a, such also being a liquid-tight enclosure as will be seen. The reactant liquids A and B are admixed by unseating and opening the valve 25 which normally frictionally engages and seals the inner container open end 24a, whereupon the liquid A flows into the liquid B. The valve 25 is opened by downward movement of the valve stem 26, after removal of the cotter pin 26a, and it will be noted that the polymerizing reaction is initiated from the exterior of the package 20 in view of the exterior projection, above the top closure 22, of the upper end 26b of the valve stem 26. Hence, the valve stem 26 may also be referred to as the package activator rod.

After the reactant liquids A and B have been mixed in the lower region 32, the package 20 will be inverted so as to pour the mixed and now curing liquid into the hollow core region 33 of the cylindrical tape spool 28, whereupon the package will be spun in the inverted position to centrifuge the liquid through the tape spool 28 and tape 29 to completely wet the latter therewith. However, by comparison of FIGS. 2 and 3 it will be understood that the upwardly facing closed end wall 24b of the inner container 24 has an axially projecting annular sealing ring 34 which is frictionally received within a comating aperture formed by a flanged rim 35 of the partition wall member 27, and it will be noted that inner container 24 must be moved away from such seating engagement in order to open the central aperture of the partition wall 27 to permit the liquid to pass therethrough and into the spool core region 33. It will also be noted that the valve stem rod 26, which is attached as by serrations 26c at its lower end 26d to a central boss 25a of the valve 25, passes through an apertured central boss or collar 36 at the center of the inner container end wall 24b. The valve stem 26 extends upwardly therefrom through a central collar 37 of the top closure 22, with which it has a sliding, though liquid-tight fit. Thus, although in order to open the valve 25 the valve stem 26 must slide through the inner container closed end collar 36, the valve stem has a friction fit within the collar 36 which is tighter than the friction fit between the inner container annular ring 34 and the partition wall flange 35 so that, upon downward movement of the valve stem 26 in response to pressure on its upper end 26b, the entire inner chamber 24 will be moved downwardly out of engagement with the partition wall member 27 before the inner container valve 25 is opened. Thus, liquid flow communication between the lower region 32 of the outer container and the spool core region 33 is established before the valve 25 is opened.

It will also be noted that the partition wall member 27 includes an inverted funnel-shaped portion 38 which widens in the downward direction and includes an outwardly projecting peripheral portion 38a which engages the interior periphery of the side wall 21b of the outer container 21, and at its upper end 38b supports the tape spool 28. Thus, the outer surface 38c of the funnel-shaped portion 38, together with the substantially cylindrical surrounding container structure at the outer periphery of the lower projecting portion 38a, forms a substantially V-shaped excess liquid collecting region 40 for receiving the excess of the centrifuged liquid reactant material, as will be further described.

Rather than forming the partition wall 27 integrally with the side wall 21b of the outer container 21, the partition wall 27 is actually formed by a lower end wall of a container-like partition structure 41 whose upwardly projecting side wall 41a lies contiguously against the inner surface of the outer container side wall 21b and whose outwardly projecting peripheral rim 41b at its upper open end seats against the similarly projecting mouth rim 21c of the outer container 21. Thus, the position of the wall portion 27 is fixed, as intended. Along the outer periphery of the outer container rim 21c is an upwardly extending peripheral portion 21d which guards the top cover 22, handle 23, and cotter pin 26a against premature displacement. Thus, in the preferred embodiment, the outer periphery of the excess liquid collection region is actually defined by the interior surface of the partition wall structure side wall 41a, although the wall portion 41a substantially coincides with the interior of the side wall 21b of the outer container 21.

Completing the description of the top closure 22 and the tape spool 28, FIG. 2 shows that the tape spool extends between the horizontal annular ring portion 38b of the partition wall 27 and the underside of the top closure 22, thus forming a peripherally extending liquid extraction region 42 surrounding the tape spool and tape 29 in view of the smaller diameter of the tape spool 28 as compared with the diameter of the peripherally surrounding container side wall 41a.

Referring to FIG. 3 the tape spool 28 has cylindrical cage-like structure defined by the several narrow and parallel annularly spaced apart cage rods 443 which extend between the flat upper and lower end rings 44, 45 along their interior circumferences. Of course, a suitable mesh-like structure might be substituted for the cylindrically arranged cage rods 43. Two opposed cage rods 43a have a plurality of outwardly projecting thicket-like prongs 43b along their lengths to facilitate retention of the tape 29 on the tape spool.

Projecting above the upper end ring 44 of the tape spool 28 is an opposed pair of cover connection pieces 46 which serve to frictionally engage a downwardly projecting annular ring 47 (FIG. 2) at the underside of the cover 22 to connect the tape spool 28 to the cover for ultimate removal with the cover when the package is opened. The underside of the tape spool 28 as defined by its end ring 45, slidably surrounds the narrow neck aperture defining ring 35 of the partition wall 27 to facilitate such removal of the tape spool.

The annular rings 47 of the closure 22 forms one sidewall of an upwardly projecting annular channel area 48 of the closure, within which the closure connection pieces 46 of the tape spool are received, as will be understood from FIG. 2. The otherwise flat central area 22a of the closure 22 is reinforced, as by radial gussets 49, against flexure, and has an upwardly projecting peripheral rim 22b which fits snugly within the open mouth of the wall structure member 41 as also seen in FIG. 2. The closure 22 also has an outwardly projecting peripheral rim 22c which seats against the similar rim 41b of the wall structure member 41.

As best seen in FIGS. 4 and 5, the outwardly projecting peripheral rim 22c of the closure 22 includes opposed handle receiving structures 50, one on each side of the closure, each including a laterally projecting handle pivot pin 51 on which the respective end loops 23a of the handle 23 are mounted. The handle loop 23a includes a tangential extension portion 23b, substantially aligned with, or preferably a distance equal to the loop diameter below the plane of the C-shaped main handle portion. When the handle 23 is aligned flat against the cover 22 as seen in FIGS. 1 and 2, the tangential extension 23b lies flat against the outwardly projecting peripheral rim 41b, the handle receiving structure 50 being displaced upwardly, as at upward recess 52, to receive the extension 23b, as best seen in FIGS. 2 and 4. Referring to FIGS. 4 and 5, the length of the extension 23b is greater than the vertical height between the rim 41b and the top of the outer container peripheral rim 21d so that, when the handle is lifted in the direction of the arrow in FIG. 5 the extension 23b acts as a lever to loosen and lift the closure 22 straight up out of its snug fit engagement with the mouth of the container.

Returning now to the manner in which the valve 25 is opened to permit the reactant liquid A in the inner container 24 to admix with the reactant liquid B, after the downward movement of the valve stem 26 has disengaged the inner container 24 from the partition wall aperture ring 35 as previously described, an outwardly extending peripheral rim 55 which surrounds the downwardly facing open end 24a of the inner container 24 abuts against the upper edges 56a of a series of annularly spaced apart support ledges 56 which project upwardly from the outer container bottom wall 21a and radially inwardly from the upwardly projecting peripheral sidewall 21b, as illustrated in FIG. 6, whereupon further downward movement of the valve stem 26 unseats the valve 25 from its snug fitting engagement within the mouth of the inner container 24. Regarding the seating of the valve 25, the valve has an annularly extending and outwardly projecting retainer ring 25b which fits snugly within the mouth formed by the downwardly facing open end 24a, and an outwardly projecting peripheral portion 25c of the valve seats against the adjacent rim 55 of the inner container 24, thus forming a liquid-tight seal. Regarding the manner in which the valve 25 opens, it will be noted that the diameter of the valve periphery 25c is smaller than the diametral spacing between the vertical inner edges 56b of any two opposed support ledges 56.

To assist the mixing action of the reactant liquids as will take place within the lower region 32, the outer container 21 further includes integrally formed and radially inward projecting vertical paddles 57, these being annularly spaced apart and located alternately between the support ledges 56, as best seen in FIG. 3. As shown in FIGS. 2 and 3, the outwardly projecting lower rim 55 of the inner container 24 is notched, as at 55a, at each peripheral location therealong corresponding to the location of a paddle 57 along the interior of the outer container sidewall 21b so that the inner container 24 is free to move vertically with respect to the paddles 57, but not in circumferential direction with respect thereto. It will be noted that the paddles 57 are parallel to the central axis of the package 20, with which the valve stem 26 coincides, and that they extend substantially between the bottom wall 21a of the outer container and the partition wall 27.

As illustrated in FIG. 7, mixing of the reactant liquids within the region 32 is performed by intermittently rotating the package 20 about its central longitudinal axis while the axis is tilted at an oblique angle, preferably 45°, to the horizontal. Although the mixing might be done at slower rotational speeds, it has been found that about six to sixteen spinning bursts of short duration, perhaps one to two seconds, on a spin table designed to achieve 2200 r.p.m. but which, because the short time duration, never achieves such rated speed, causes thorough mixing of the reactants. Tilting of the package and the presence of paddles 57 prevent centrifugal hang-up of the liquid, and assists the mixing action.

After mixing is completed so that the polymerizing reaction has commenced, the still unopened package 20 is further tilted to the 180° position in which it is inverted as illustrated in FIG. 8 whereupon, within a few seconds, the mixed liquid flows via the funnel 38 through the partition wall opening formed by the funnel neck ring 35, and into the core region 33 of the cylindrical tape spool 28. After a few seconds to permit such flow, the package 20 is again spun on its central axis, this time at 2200 r.p.m. for five seconds, which causes the liquid within the core region 33 to be centrifuged through the interstices of both the tape spool 28 and the liquid-pervious tape material 29 to thoroughly and uniformly wet the tape 29. To ensure thorough wetting an excess of liquid is provided, much of which emerges from the outer periphery of the spool of tape into the extraction region 42 therethrough. However, some liquid may remain within the core region 33 of the tape spool.

After the wetting step the package is uprighted as shown in FIG. 9, in which position it is permitted to remain stationary for a few seconds to permit draining of any liquid from the tape spool core region 33 back through the funnel opening 35 to the bottom of the outer container 21 where it collects, and to permit downward draining of the excess liquid from the peripheral wall 41a and the underside of the cover 22 into the excess liquid collection region 40. The package is again spun at 2200 r.p.m. on its central axis to remove by centrifugal extraction excess liquid remaining within the tape 29 as would otherwise seal the interstices of the tape material. Such excess liquid is initially deposited on the peripheral wall 41a and, after the spinning has stopped, will also collect in the liquid collection region 40.

After such extraction, the liquid impregnated or coated tape material is damp to the touch, and is ready for winding on the patient's body member to form an orthopedic cast. As previously noted, the liquid is in a curing state, and will harden within about ten minutes.

Referring briefly again to FIGS. 4 and 5, the package 20 is now opened by lifting the handle 23 to remove the top closure 22 which, as illustrated in FIG. 10, carries with it the now wetted spool of tape 29.

Referring to FIGS. 10–12, the plastic mesh tape retaining band 30 has at one of its ends a slotted eyelet piece 60, the slot being indicated by reference numeral 60a, by which it is connected to its opposite end which carries the finger tab 61 and includes a rod-like adjustment length portion 62 which is received in the eyelet 63 of the eyelet piece 60, via the slot 60a. The tightness of the band 30 around the spool of tape 29 is adjustable by means of the knobs 64 which are integrally formed on the rod-like extension 62 and have diameter larger than the eyelet 63.

When the wetted spool of tape has been removed from the package as shown in FIG. 10 the tape spool 28 may be separated from the cover 22 by grasping its lower flange ring 45, the cover 22 continuing to be held in the other hand. Alternatively, the physician may prefer to unwind the tape from the spool while the spool remains connected to the cover as shown in FIG. 10. In either case, the physician first removes band 30 by grasping the finger tab 61 and pulling the extension portion 62 back through the eyelet slot 60a. As illustrated in FIG. 13, the physician then winds the wetted tape on a body member of the patient, such as his arm 65, applying the tape directly from the spool 28. As illustrated in FIG. 14, it is believed that winding to provide three layers of the tape on the patient's limb will be adequate to form an extremely effective orthopedic cast 66. Although not illustrated, it should be understood that the patient's body member will be initially covered with a knitted sleeve or the like, so that the resin does not contact his skin.

Referring now to FIGS. 17–19 it will become apparent that, by using several differently configured top closures with or without a spacer spool 70 (FIGS. 17 and 19), and by lengthening the valve stem 26 if necessary (FIGS. 18 and 19), the same package 20 may accommodate tapes of different widths. That is, as previously mentioned, the tape spool 28 illustrated in FIG. 2 has 2" wide tape wound thereon. If a 1" wide tape is to be packaged, FIG. 17 illustrates that the same top closure 22 would be used, but that a nominally 1" wide (i.e., 1" high) spacer spool 70, having a lower end ring 71 to be received over the partition wall ring 35 and an upper end ring 72 matching the wall ring 35, would be interposed between the underside of the 1" tape spool 73 and the partition wall portion 38b.

A high crown closure 74 as illustrated in FIGS. 18 and 19 is substituted for the closure 22 when either a 3" wide tape (FIG. 19) or a 4" wide tape (FIG. 18) is to be packaged. In FIG. 19, the underside 75 of the 3" high tape spool is seated on the upper end ring 72 of the spacer spool 70 whereas, as shown in FIG. 18 no spacer is needed for the 4" high tape spool whose underside 76 is seated directly on the partition wall portion 38b, as in the FIG. 2 embodiment.

Excepting for its 2" higher central crown portion 77, the high crown closure 74 has substantially the same features as the closure 22. That is, it has an upwardly projecting annular channel ring 48 into which the cover connection pieces 46 of the 1", 3" and 4" tape spools are snugly received, as shown, and the closure 74 fits within the open mouth at the upper end of the wall partition structure 41, as in the case of closure 22. Although not illustrated, the high crown closure 74 has a handle similar to the handle 23, including a convenient closure removal feature similar to that shown in FIGS. 4 and 5. Moreover, it should be noted that the upwardly projecting peripheral wall of the crown portion 77 has a diameter substantially larger than that of the 3" and 4" high tape spools in order to provide an excess liquid extraction region 78 within the crown, which is an upward continuation of the extraction region 42 within the upper region of the package above the partition wall 27.

As previously described in connection with FIGS. 6-9, an orthopedic cast-making package in accordance with the invention is intended to be activated on the scene, where the patient is being treated. Accordingly, it is contemplated that the activating steps previously described will be performed on the package by an activator machine, such as the machine 80 which is diagrammatically illustrated in FIGS. 15 and 16, and which would be available as a part of the general equipment of the hospital or physician's office.

Briefly, and referring first to FIG. 15, the package 20 is placed on a spin table 81 of the machine which is rotated by a spin motor 90 via the pulley belt 91. A toggle clamp 82, which is manually operated by the handle 83, presses the package 20 downwardly thereagainst. Excepting for its vertically movable clamping head 84, the clamp 82 is mounted in fixed position on a bracket 82a which projects forwardly from a tilt frame 85 to which the bracket is attached. The spin motor 90 is also mounted on the tilt frame 85, but on its rearward side.

From the position of the clamp 82 in alignment with the upwardly projecting end of the package valve stem 26, it will be understood that downward movement of the clamping head 84 moves the stem 26 downwardly, and activates the package by permitting the reactant liquids A and B to admix with each other. It will also be noted from FIGS. 6-9 that downward clamping of the package against the spin table 81 is actually via the valve stem 26 and opened valve 25 which presses against the bottom wall 21a of the package.

FIG. 16 shows the three positions of the package 20 during the mixing, wetting, and extraction steps of the invention, the mixing and tape wetting positions being shown in phantom lines and designated 20a and 20b, respectively. The initial placement position of the package 20 and the same position for the extraction step is shown in full lines. The tilt frame 85 is rotated between these three positions by a tilt motor (not shown), at each of which the tilting is stopped.

Thus has been described an orthopedic cast-making package and method for preparing orthopedic cast-making materials for use, which achieves all of the objects of the invention.

What is claimed is:

1. In combination, a spool, an orthopedic bandage comprising a flexible carrier of liquid pervious material wound on itself about said spool, and a minimal but adequate coating on said bandage of a curing solid-resin forming liquid composition comprising a mixture of 100 parts by weight of methylene diphenyl diisocyanate, 50 parts by weight of the reaction product of glycerine and propylene oxide having an average molecular weight of approximately 260, dibutyl phthalate as a plasticizer and from about 0.03 to about 0.30 parts by weight of dibutyl tin dilaurate as a catalyst, whereby said carrier becomes rigid throughout upon completion of said curing.

* * * * *